(12) United States Patent
Scatizzi

(10) Patent No.: US 6,588,464 B2
(45) Date of Patent: Jul. 8, 2003

(54) APPARATUS FOR THE AUTOMATED PREPARATION OF SOLUTIONS AND A COMBINED SYSTEM FOR METERING LIQUID PRODUCTS, SOLID PRODUCTS AND SOLUTIONS

(75) Inventor: Mario Scatizzi, Pistoia (IT)

(73) Assignee: Tecnorama S.r.l. (IT)

( * ) Notice: Subject to any disclaimer, the term of this patent is extended or adjusted under 35 U.S.C. 154(b) by 3 days.

(21) Appl. No.: 09/892,030

(22) Filed: Jun. 26, 2001

(65) Prior Publication Data

US 2002/0004020 A1 Jan. 10, 2002

(30) Foreign Application Priority Data

Jul. 6, 2000 (IT) .................................. FI2000A000153

(51) Int. Cl.[7] .................................................. B65B 1/04
(52) U.S. Cl. ...................... 141/130; 141/104; 141/168; 422/99; 422/100
(58) Field of Search ..................... 141/130, 250, 141/104, 9, 100, 67, 129, 165, 168, 171, 176, 181, 183, 187, 234, 238, 242, 243, 247, 387; 422/99, 100

(56) References Cited

U.S. PATENT DOCUMENTS 6,105,636 A * 8/2000 Scatizzi et al. ............. 141/130
6,302,168 B1 * 10/2001 Hu .............................. 141/104

FOREIGN PATENT DOCUMENTS

EP          0 897 031 A2      2/1999

* cited by examiner

Primary Examiner—Steven O. Douglas
(74) Attorney, Agent, or Firm—McGlew and Tuttle, P.C.

(57) ABSTRACT

An apparatus for the automated preparation of solutions with combined metering system is provided with a structure with a platform (1) upon which it is possible to position one or more containers for solid products, one or more bottle-like containers for liquid products, one or more containers for solutions and one or more empty and clean bottle-like containers. A carriage (2) is movable onto the platform (1). An apparatus is associated with the carriage (2), for the removal and handling of the bottles and for the removal, handling and actuation of at least the containers for solid products. An apparatus (6) is provided for preparing solutions and/or mixtures starting from the solid substances.

20 Claims, 11 Drawing Sheets

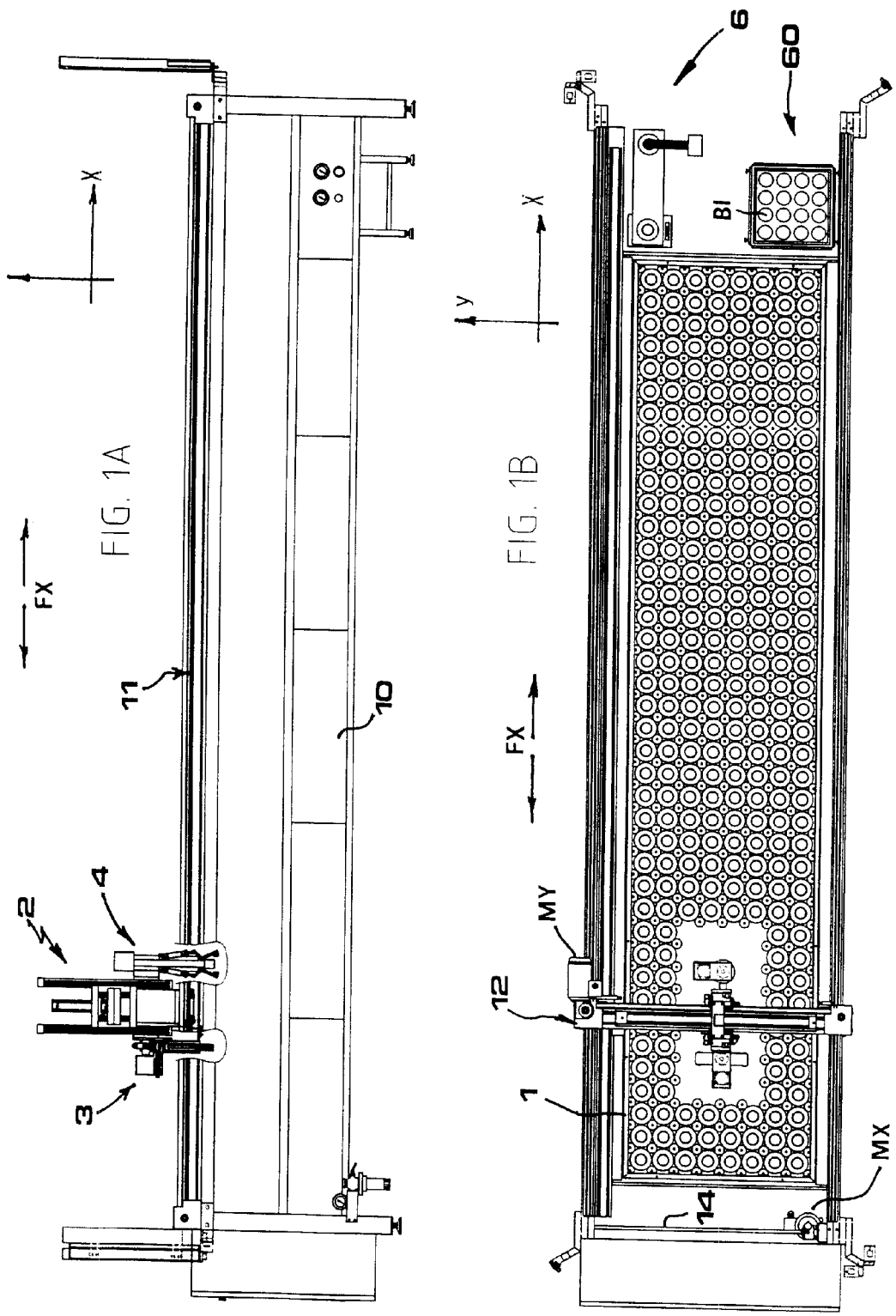

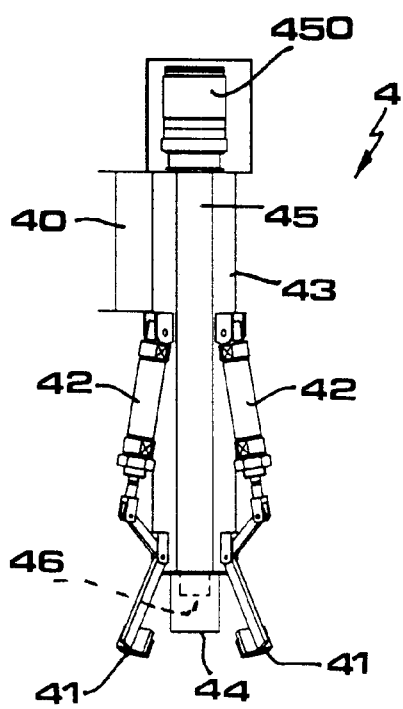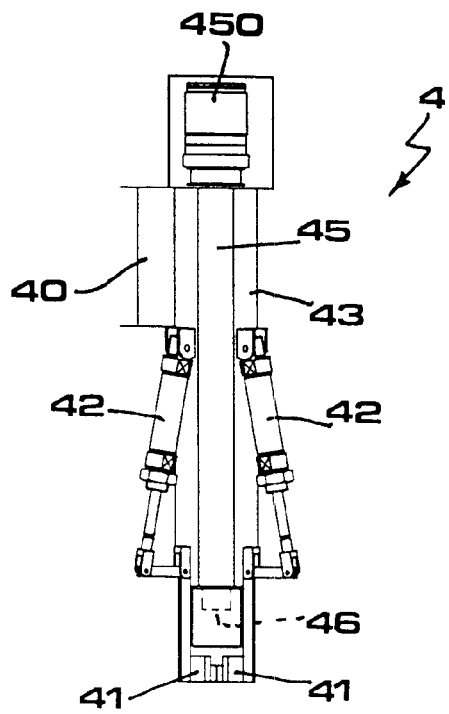
FIG. 3A  FIG. 3B
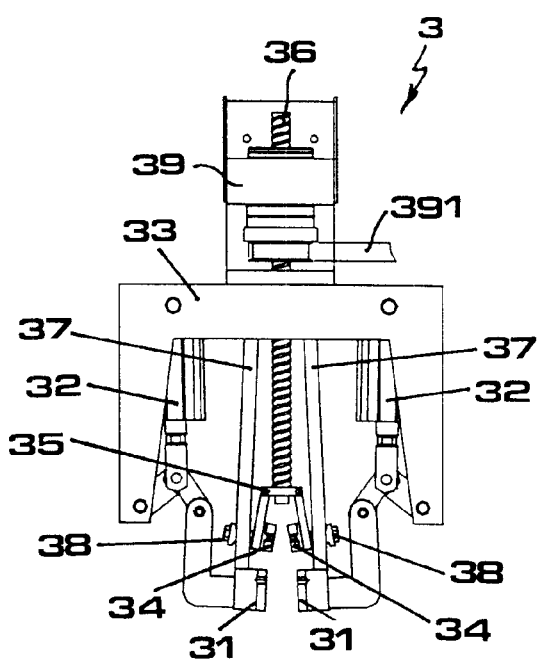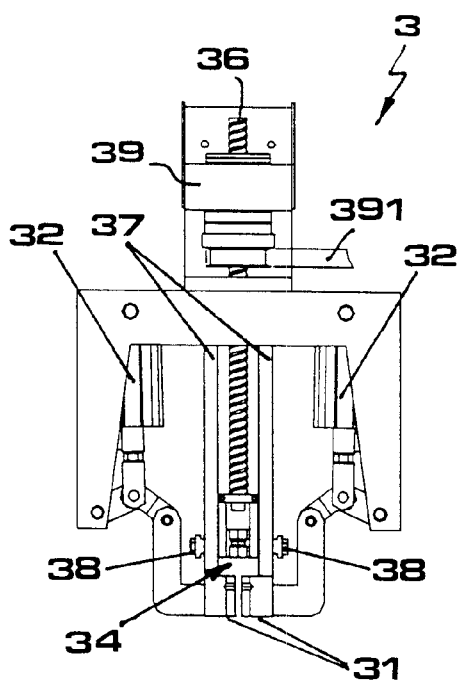
FIG. 4A  FIG. 4B

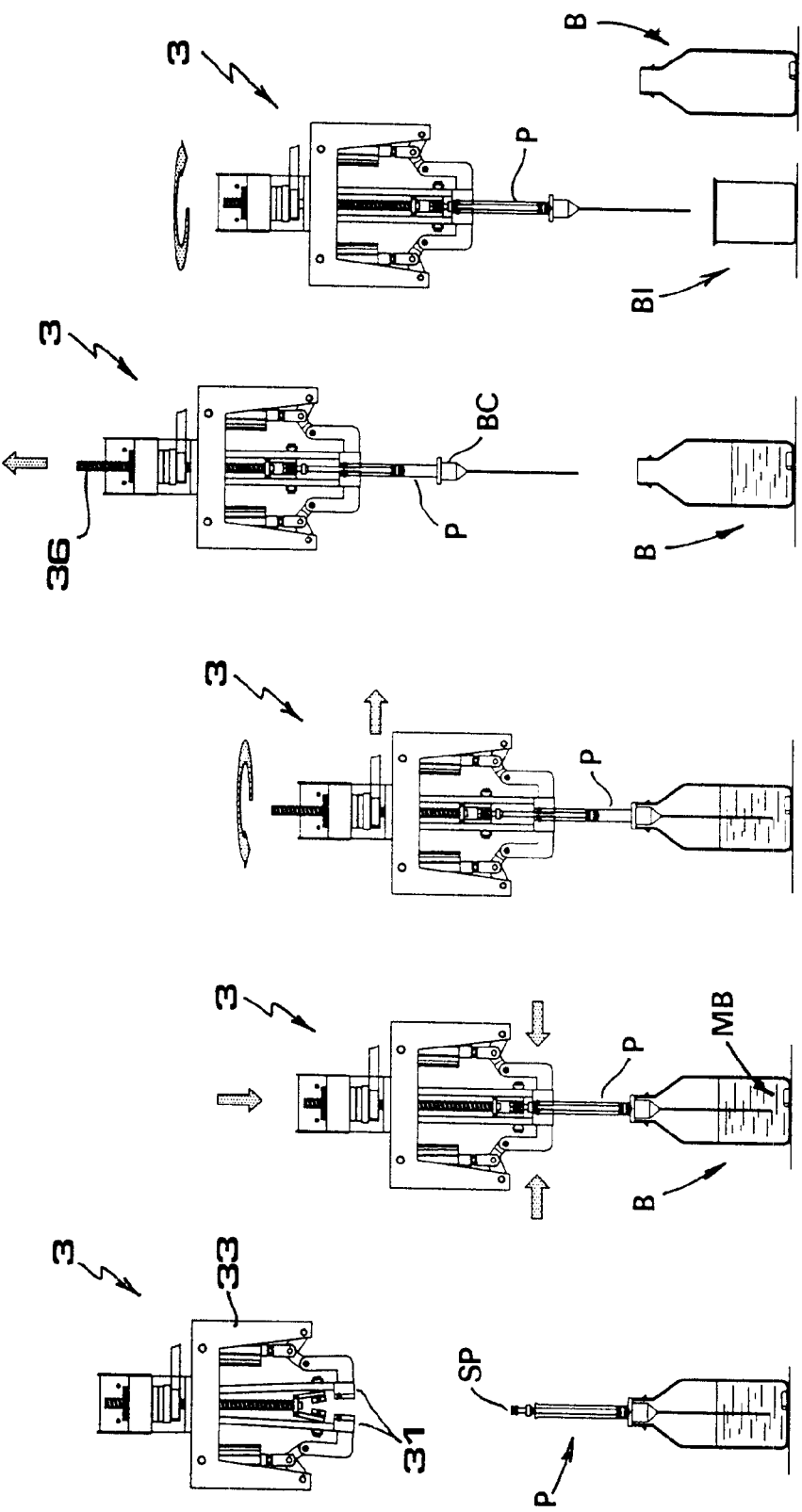

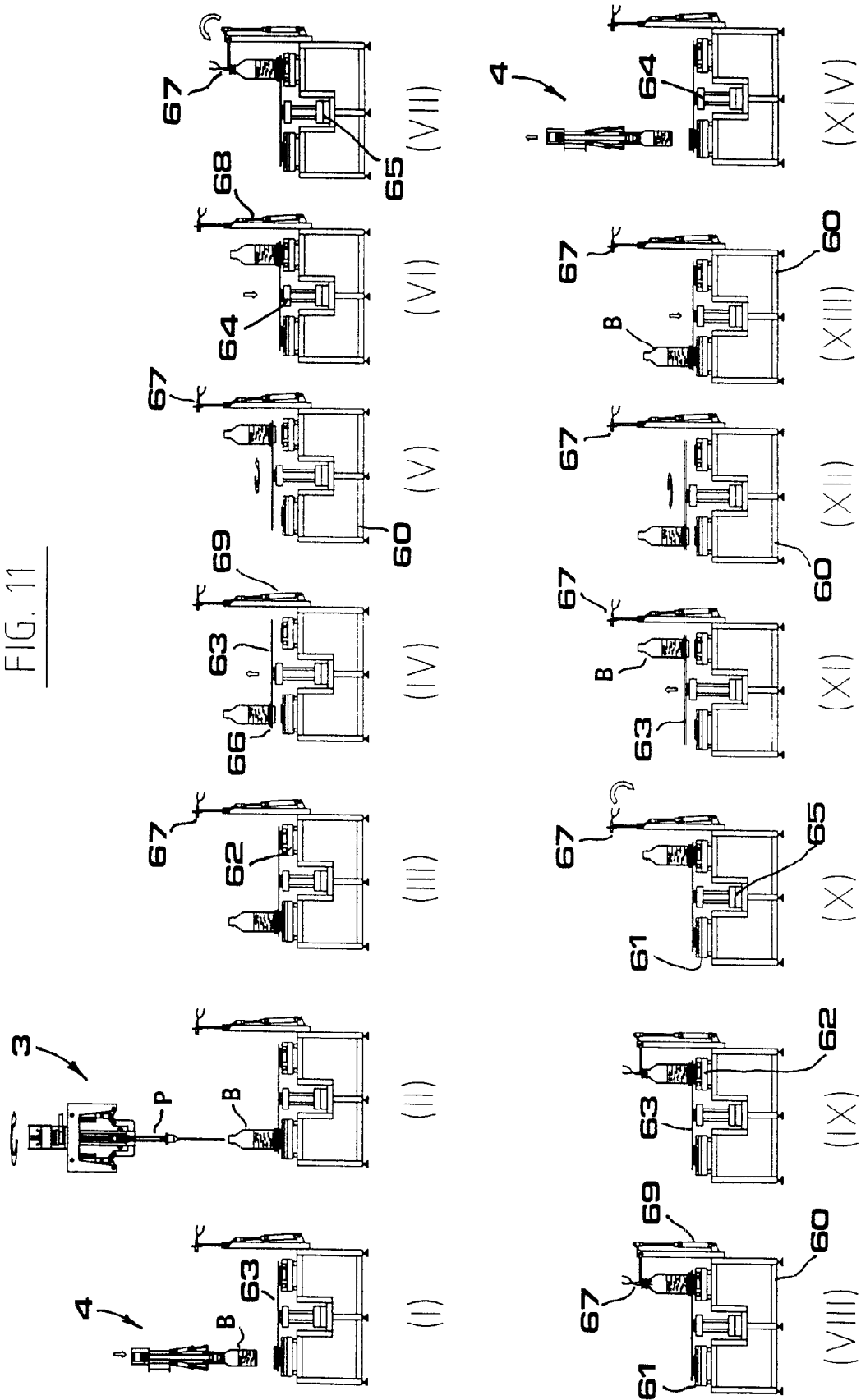

APPARATUS FOR THE AUTOMATED PREPARATION OF SOLUTIONS AND A COMBINED SYSTEM FOR METERING LIQUID PRODUCTS, SOLID PRODUCTS AND SOLUTIONS

SPECIFICATION

The present invention refers to an apparatus for the automated preparation of solutions and a combined system for metering liquid products, solid products and solutions.

Colouring solutions for the so-called "colour laboratories" of the textile industry, in which tests are carried out on the effects of the solutions over fabrics to be dyed, are known to be prepared according to a process which until now has required a massive and instrumental intervention of human operators.

In particular, the operators prepare the solutions by manually metering the liquid or solid products to be dissolved into water or other. This operation is carried out each time a solution becomes exhausted or expires for having left unused for too long. For example, in case of solutions obtained from powdered or granulated products, the operator takes a container in which to prepare a solution, places it on a plate of a precision scale and puts on it firstly the products to be dissolved and then the water or other solvent. Thereafter, places the container with the thus prepared solution onto the platform of an apparatus for the removal and metering of the solutions. Such an apparatus is described in EP 897.031.

This procedure may brings about errors of some importance: the manual metering of the products to be dissolved may be affected by inaccuracies also of significant level and, moreover, the operator can place the container at a location other than the one being preset upon the structure's platform for removing and metering the solutions.

The same drawbacks may result also in other industrial sectors, in which provision is made for using solutions to be delivered and metered by automated systems.

The main object of the present invention is to overcome the said drawbacks.

This result has been achieved, according to the invention, by providing an apparatus having the features indicated in the characterizing part of claim 1. Further characteristics being set forth in the dependent claims.

The present invention makes it possible to automate the steps related to the preparation of the titrated solutions, that is, to the metering of the products to be dissolved and to the dissolution of same products into the required volume of solvent. Moreover, a single apparatus is able to operate automatically both the steps of preparation of the solutions and those relevant to the metering of the solutions thus prepared. Moreover, it is possible to control, also automatically, the metering of liquid and solid products and solutions as well to achieve mixtures formulated according to predetermined "recipes". A further advantage offered by the present invention lies in the relative constructional and functional simplicity of the apparatus.

These and other advantages and characteristics of the invention will be best understood by anyone skilled in the art from a reading of the following description in conjunction with the attached drawings given as a practical exemplification of the invention, but not to be considered in a limitative sense, wherein:

FIGS. 1A and 1B are a side view and a plan view of an apparatus according to the invention;

FIGS. 3A and 3B show schematically the clamp unit for the bottles and containers of the powdered and granulated products, with open (FIG. 3A) and closed (FIG. 3B) jaws;

FIGS. 4A and 4B show schematically the clamp unit for the pipettes, with open (FIG. 4A) and closed (FIG. 4B) jaws;

FIGS. 5A–5E show schematically a succession of steps relating to the removal of a solution from a bottle and to the metering thereof into a glass;

FIG. 11 shows schematically a succession of steps relating to the preparation of titrated solutions obtained from liquid products;

In the description that follows, the terms "liquid products" and "solid products" refer to substances in the liquid state and in the solid state (powder, crystals or granules), respectively, with which the "solutions" are prepared. The term "mixtures" refer to substances obtained by mixing, according to preset formulae, one or more solid or liquid products and solutions. The "mixtures" and "solutions" representing the end product of the process.

Figure 1C:
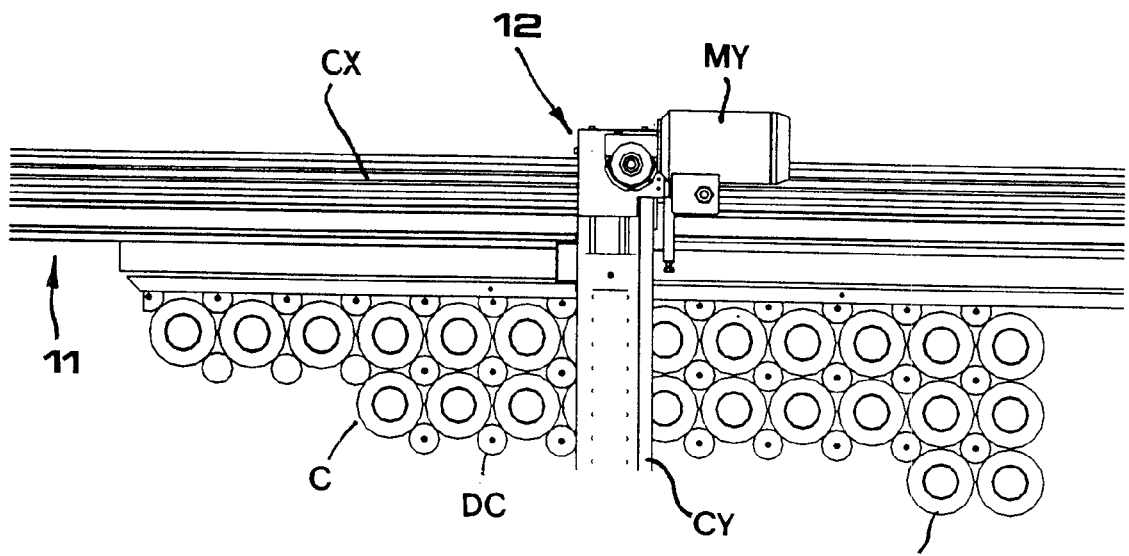
FIGS. 1C and 1D show enlarged details of the drawing of FIG. 1B.
Figure 1D:
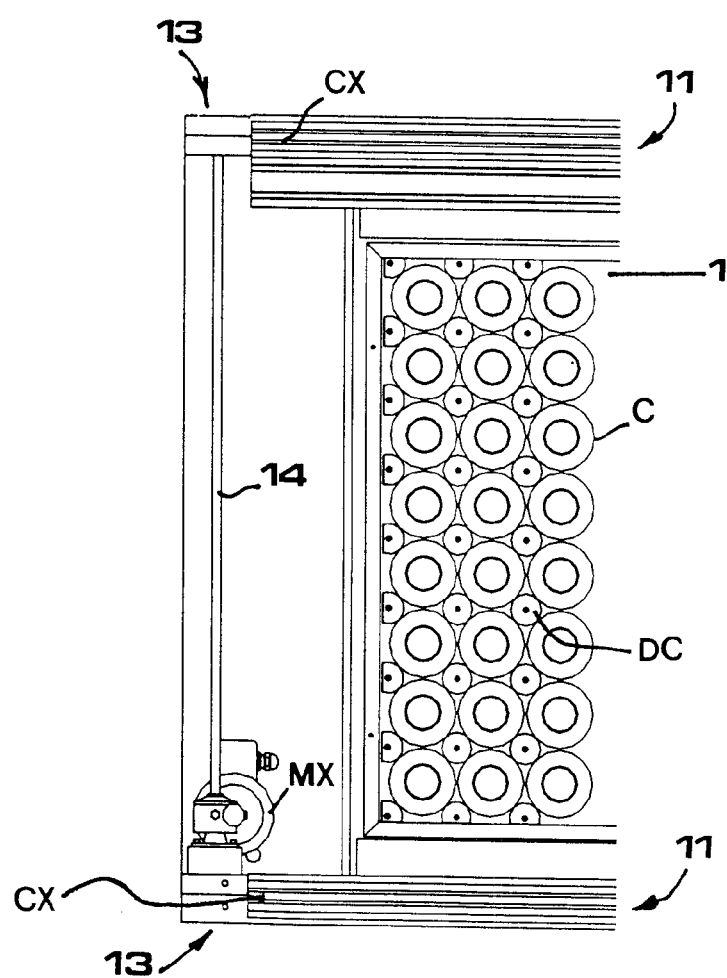

Reduced to its basic structure, and reference being made to the figures and the attached drawings, an apparatus according to the invention comprises:

a structure with a platform (1) upon which it is possible to position one or more containers for solid products, one or more bottle-like containers for liquid products, one or more containers for solutions, one or more empty and clean bottle-like containers; each of said containers being positioned at a known and preset location of the platform (1); in the drawing of FIGS. 1B, 1C and 1D, the containers for solid products, for liquid products and for the solutions are all depicted alike and designated with the same symbol for the sake of clarity; the said containers being kept in the respective positions by means of cylindrical spacers (DC) emerging vertically from the platform (1).

a carriage (2) movable onto said platform (1) along both the axes (x, y) of planar development of the latter;

means (3), associated with said carriage (2), for the removal, handling and actuation of pipettes (P) apt to the removal and delivery of said liquid products and said solutions;

means (4) associated with said carriage (2) for the removal and handling of said bottles (those for liquid products, those for the solutions and the empty bottles as well) and for the removal, handling and actuation of said containers for solid products;

means (6) for preparing solutions starting from said liquid and solid substances: said means (6) being provided in a corresponding station downstream of the platform (1);

programmable means (UE) for driving the carriage (C), the said means (3) and means (4).

Said platform (1) rests, at a predetermined height from the ground, upon a supporting structure (10). Mounted on two opposite sides of this structure are corresponding straight guides (11) onto which a bridge element (12), apt to support the said carriage (2), slides. Said guides (11) extend in a direction of the longitudinal axis (x) of platform (1). Said element (12) extends orthogonally to said axis and rests upon two vertical stays whose bases are slidingly mounted on said guides (11).

An electric motor (MX), controlled through the programmable unit (UE) by means of an encoder, for example, is provided for moving the bridge (12) along the guides (11)—as indicated by the arrows (FX) in FIG. 1A—via two ring-like closed belts (CX) driven out over corresponding pulleys (13). Two of said pulleys (13) are connected to an axis (14). The latter is associated with a motor (MX) and is oriented parallel to the bridge (12). The base (120) of each stay of the bridge (12) is fixed to one of said belts. In this way, the bridge (12), and thus the carriage (2) with it, results movable onto the platform (1) under control of the motor (MX), as indicated by the arrows (FX) in FIGS. 1A and 1B.

Figure 2A:
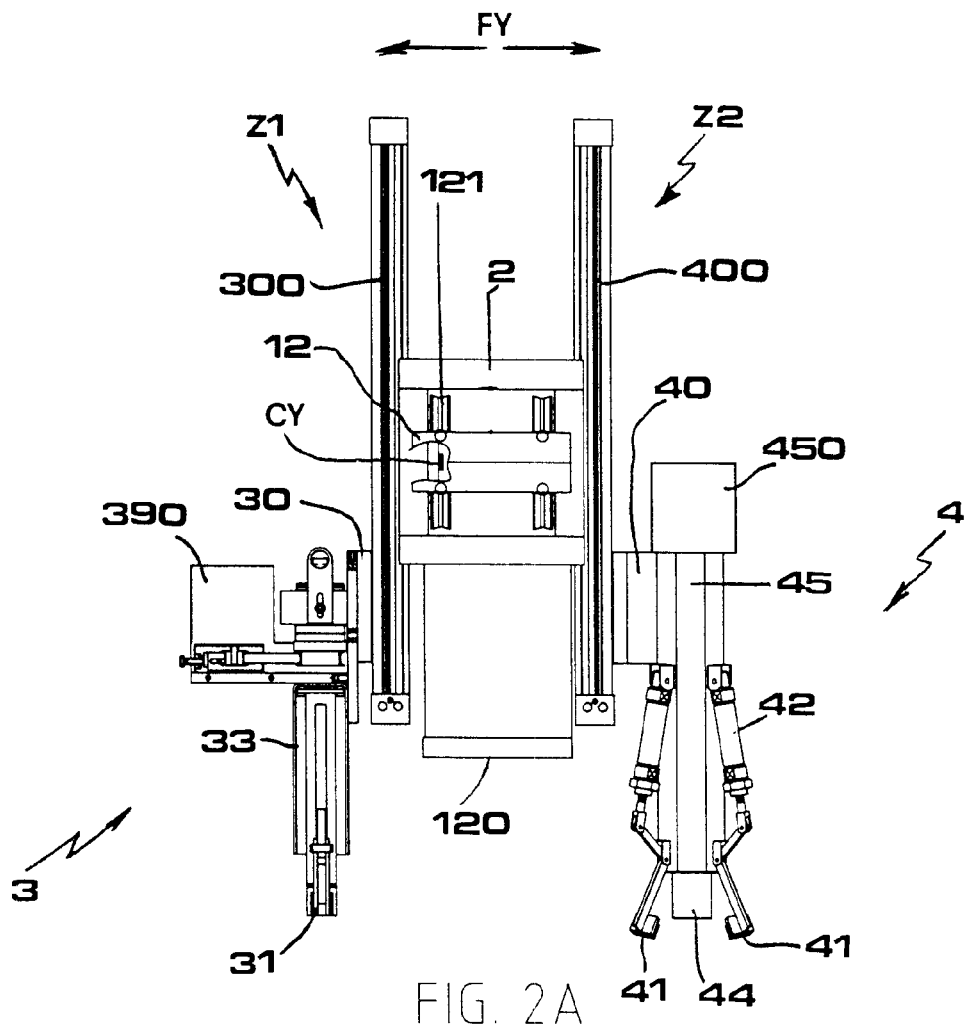
FIG. 2A shows schematically the mobile carriage assembly.
Figure 2B:
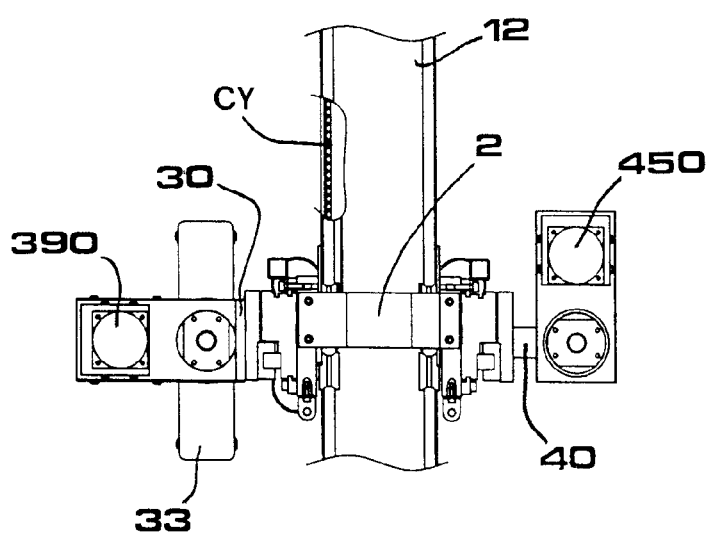
FIG. 2B is a plan view of the assembly of FIG. 2A.
Figure 6D:
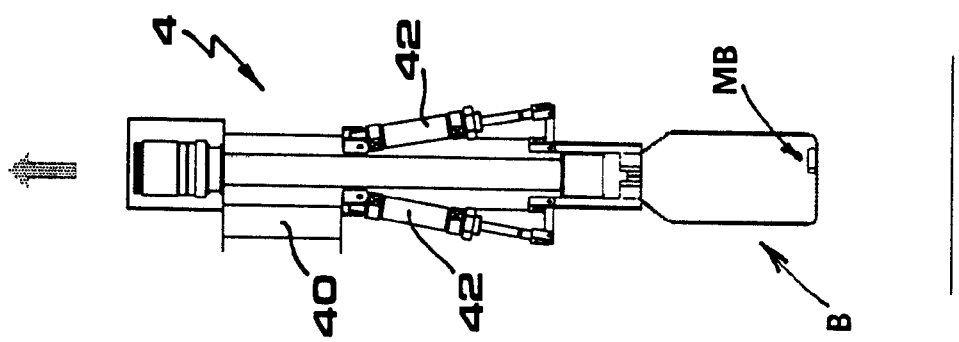
FIGS. 6A–6D show schematically a succession of steps relating to the removal and handling of a bottle.
Figure 6C:
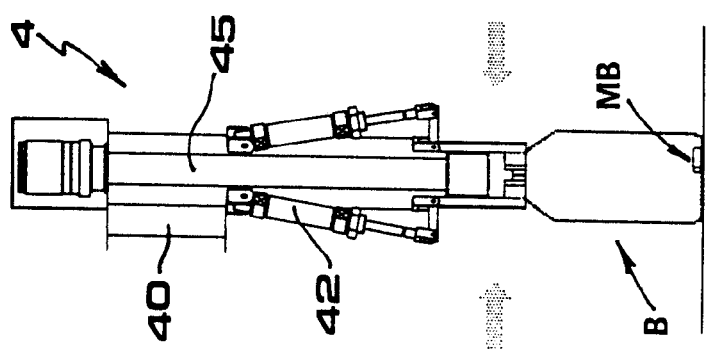
Figure 6B:
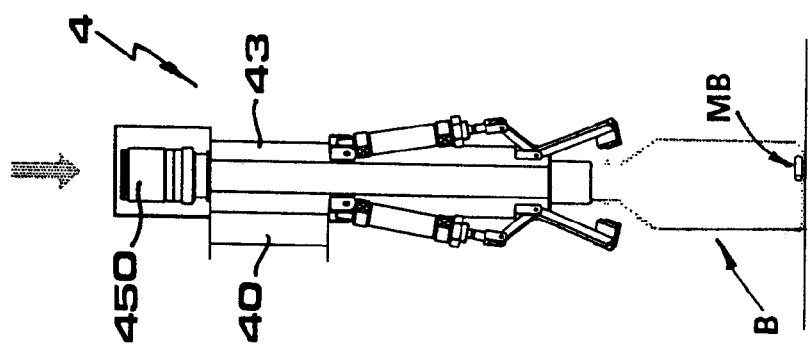
Figure 6A:
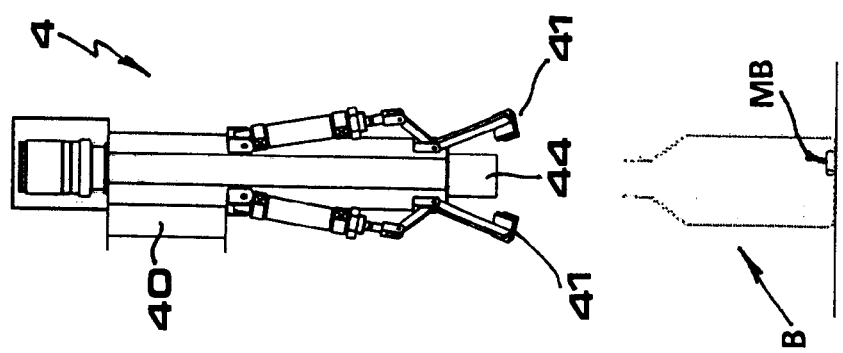
Figure 7D:
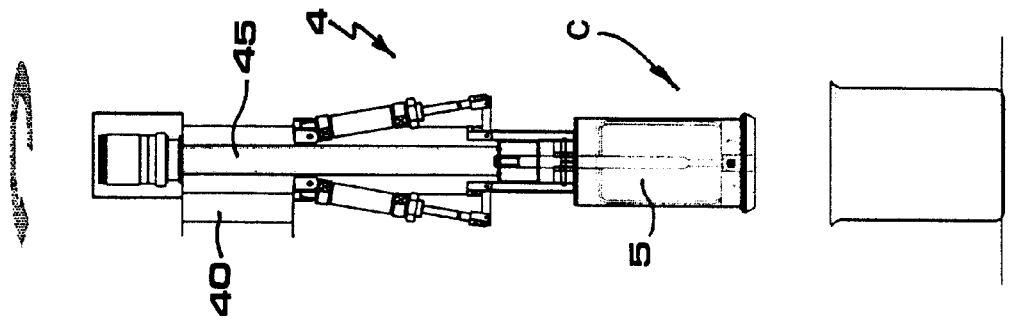
FIGS. 7A–7D show schematically a succession of steps relating to the removal, handling and actuation of a dispenser for powdered products.
Figure 7C:
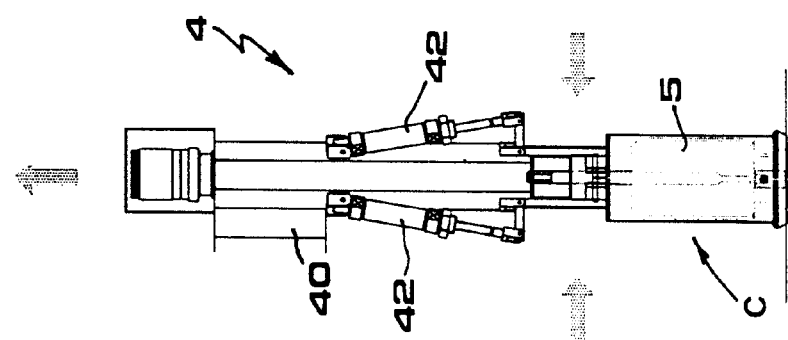
Figure 7B:
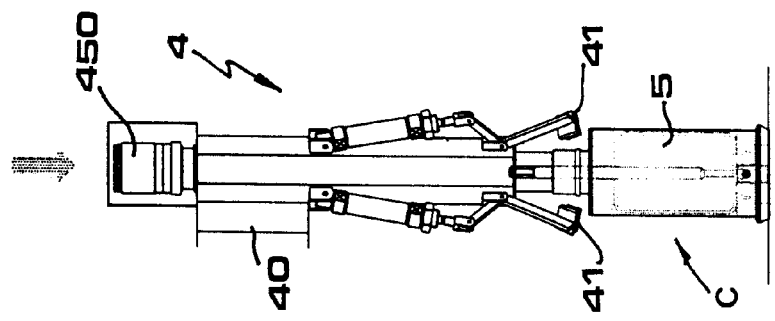
Figure 7A:
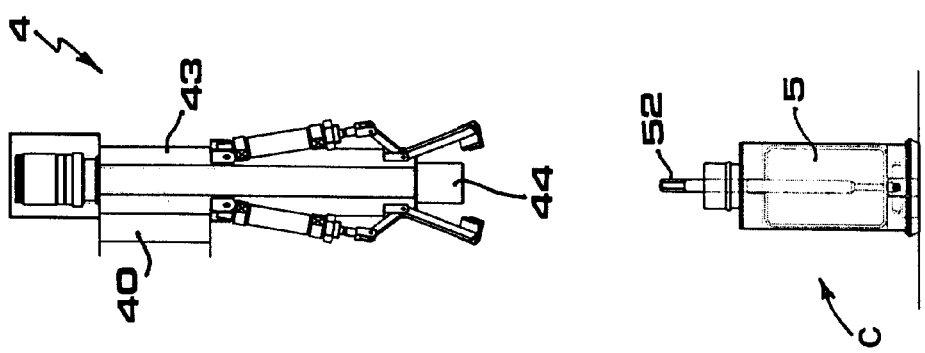

Similarly, the carriage (2) is mounted on the bridge (12) so as to result movable orthogonally to the longitudinal axis of the platform (1), as indicated by the arrows (FY) in FIGS. 1B and 2, under control of a corresponding electrical motor (MY) operated by the programmable unit (UE) through an encoder, for example. The shaft of motor (MY) is connected to at least a side of carriage (2) via a corresponding belt (CY) developing parallel to the bridge (12) and ring-like closed over two transmission pulleys. One length of said belt (CY) is fixed to the carriage (2) which rests slidingly onto the crosspiece (12) and is kept guided on the latter with the aid of needle rollers (121) provided on both its lower and upper bases.

The means (3) provided for the removal, handling and actuation of the pipettes (P), are supported by a bracket structure (30) fixed to a side of said carriage (2). Such means comprise a clamp with two jaws (31) operable by corresponding pneumatic actuators (32) through a system of levers hinged to each other and to an outer skirt (33), which acts also as a support for the actuators (32) and is supported by the bracket (30). The said jaws (31), when in the closed condition (as in FIGS. 5B–5E) provide for clamping the pipettes (P) as suitably programmed. The clamp in question comprises a further pair of jaws (34), disposed on top of the other two. Each of the upper jaws (34) is hinged to a dish (35) borne by a worm screw (36) having vertical axis. The said worm screw goes centrally through said skirt (33) and between two rods (37). These rods, on one side, are solid to the lower jaws (31) and, on the opposite side, are hinged to the skirt (33). The upper jaws (34) are also engaged with said rods (37) by corresponding anchoring journals (38). The screw (36) meshes with a lead nut (39) supported by said skirt (33) and associated with an electric motor (390) via a transmission belt (391). Said motor (390), as well as the clamp's skirt (33) and the lead nut (39), are fixed to the said bracket (30). The rotation of the lead nut (39) under control of the motor (390) causes the corresponding lifting/lowering of the screw (36), that is, of the upper jaws (34). The latter are provided (as illustrated in FIGS. 5A–5E) for engaging the piston (SP) of pipettes (P) between the lower jaws (31), and thus the lifting/lowering thereof as programmed. During the lifting and lowering steps of the piston (SP), the upper jaws (34) of the clamp are moved by means of the rods (37). The liquid products are taken in and delivered by the pipettes in amounts corresponding to the stroke imposed on the piston (SP) through the rotation of the screw (36).

The means (4) intended for removing and handling the bottles (B), and containers (C) for solid substances, are supported by a bracket structure (40) fixed to the carriage (2) on the side opposite to said means (3). The above mentioned means (4) comprise a clamp with four jaws (41) (only two of them being shown in the figures) operable by corresponding pneumatic actuators (42) by a system of levers hinged to each other and to a tubular skirt (43), which serves also as a support for the actuators (42) and is supported by the bracket (40). The said jaws (41), when disposed in closed condition (as shown in FIGS. 3B and 6A–6D) provide for clamping the bottles (B) and containers (C) as preset by the program. The skirt (43) ends up with a cylindrical bush (44) of such a diameter and height which allow it to be positioned onto the neck of bottles (B) and containers (C). Moreover, inside the tubular skirt (43) there is a shaft (45) associated with a corresponding electrical motor (450) and terminating with a power takeoff (46). The latter is inside said bush (44) and makes it possible, as best described later on, to operate the metering means which the containers (C) for solid substances are provided with. The two brackets (30, 40), which support the clamp means (3) and (4), are engaged with two corresponding vertical pneumatic actuators (Z1, Z2). Formed on the outer skirts of said actuators (Z1, Z2) are the straight guides (300, 400) for slidingly guiding the same brackets (30, 40) up and down with respect to the platform (1).

Accordingly, the clamp units (3, 4) are able to be moved in both directions (x, y) of development of platform (1) and vertically as well, from and to the plane of the latter.

Figure 8A:
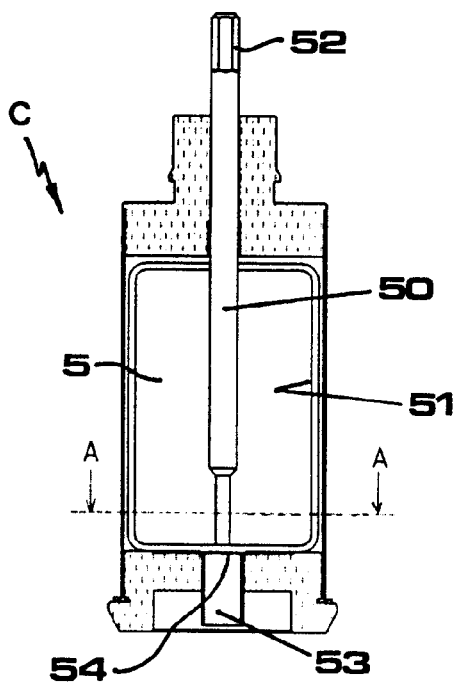
FIGS. 8A and 8B show a longitudinal section view and a cross section view of a dispenser for powder and crystal products.
Figure 8B:
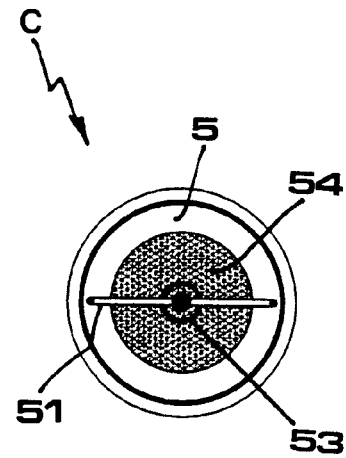
Figure 9A:
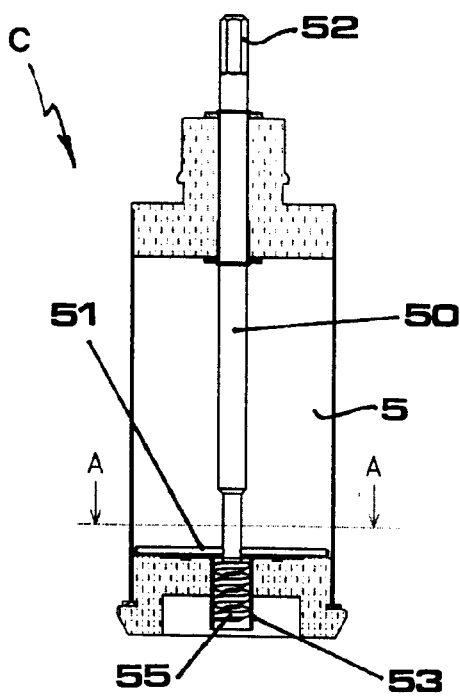
FIGS. 9A and 9B show a longitudinal section view and a cross section view of a dispenser for granule products.
Figure 9B:
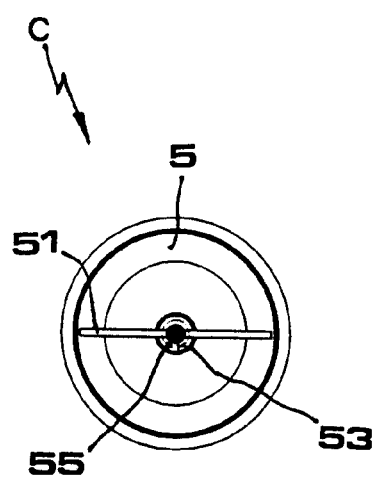

The containers (C) for solid substances may be, for example, of a type as illustrated in FIGS. 8A and 8B and/or of a type as illustrated in FIGS. 9A and 9B. In both cases, they have a chamber (5) for containing the solid substances (in the form of powder or cystals in the case of the container of FIGS. 8A and 8B, of granules in the case of the container of FIGS. 9A and 9B) and comprise a delivery device. In both cases, the delivery device for solid substances comprises a vertical rod (50) passing centrally through said chamber (5) and with which rod a scraper (51) is engaged. The free or upper end (52) of rod (50) is suitably shaped to fit into the power takeoff (46) of unit (4). In correspondence of the lower base of the chamber (50), said containers (C) exhibit a tube (53) for outputting the substances. The container illustrated in FIGS. 8A and 8B has a net (54) of close meshes between the scraper (51) and the tube (53). In the case of the container (C) illustrated in FIGS. 9A and 9B, the rod (50) terminates below with a screw feeder (55) inside said tube (53). The solid products come out of the tube (53) in amounts corresponding to the number of revolutions imposed by the scraper's rod via the motor (40).

Figure 10:
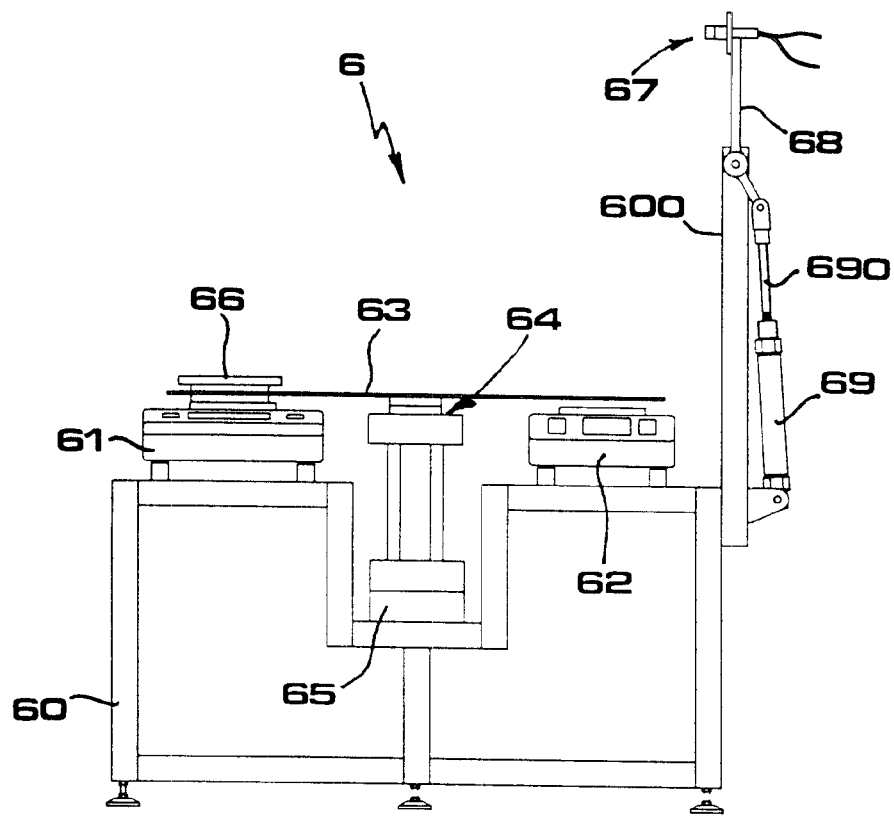
FIG. 10 is a front view of the unit for preparing the solutions.
Figure 13:
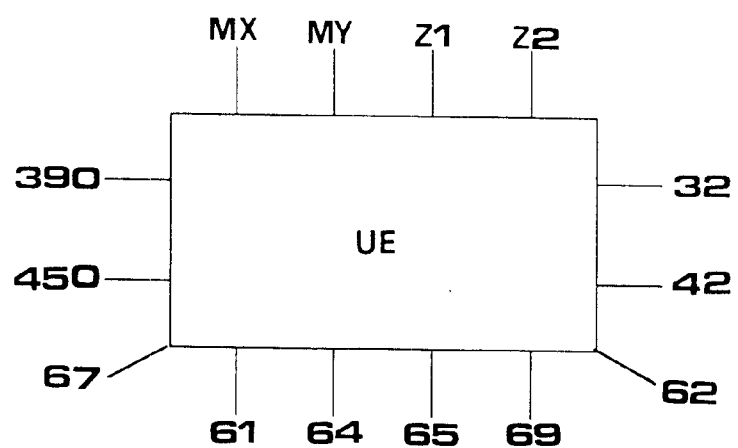
FIG. 13 is a schematic representation of the programmable control means.

As best illustrated in FIG. 10, the means (6), in correspondence of which the solutions are prepared starting from the substances conveyed by the pipettes (P) and containers (C), are disposed on a structure (60) located downstream of platform (1). Such means comprise an electronic scale (61) connected to the programmable unit (UE) and, beside said scale, a magnetic stirrer (62) able to agitate, by magnetic effect, a metal body (MB) loosely disposed inside each bottle (B). Both the scale (61) and the magnetic stirrer are known per se and, accordingly, will not be described in greater detail. Said means (6) further comprise a table (63) fixed to a rotary actuator (64) which is associated with the programmable unit (UE). The rotary actuator (64) is in turn associated with a linear pneumatic actuator (65) also connected to the programmable unit (UE). The table (65) is provided with a seat for an adapter or tray (66) in each the bottles (B) are positioned as above described. The linear actuator (65) allows lifting and, respectively, lowering the table (63) together with the adapter (66), while the rotary actuator (64) allows the positioning thereof in correspondence with the scale (61) and stirrer (62). Disposed close to the latter is a spout (67) for delivering hot and cold water or other solvents. The spout (67) is mounted at the end of a rod (68) hinged to an appendix (600) of the structure (60). The other end of the rod (68) is solid to the stem (690) of a pneumatic actuator (69) whose skirt is also anchored to the appendix (600) of structure (60). The extension movement of the stem (690) causes the rod (68) to rotate downward, with the spout (67) being thus moved to a position suited for delivering water or other solvent. Vice versa, the retraction of stem (690) drives the rod (68) into upward rotation and puts the spout (67) to an inoperative position (as shown in FIG. 10).

Described herebelow are possible modes of operation of an apparatus according to the invention. The operating steps which occur in succession, as indicated, are controlled by the programmable central unit (UE) which is, advantageously, a personal computer.

A first example relates to the preparation of titrated solutions starting from a liquid product.

Firstly, the carriage (2) is moved on to a place in correspondence of an empty and clean bottle (B). Thereafter, the unit (4) is lowered toward the platform (1) by operating the actuator (Z2) until the bush (44) results fitted on the neck of the empty bottle. At this point, the jaws (41) clamp the body of the bottle tightening the latter, and the unit (4) is lifted up, that is, moved back to its initial level, and the empty and thus retained bottle is then transported up to the scale (61). More precisely, the empty bottle is disposed within the adapter (66), as indicated in FIG. 11-I, and released from the hold of jaws (41). Afterwards, the carriage (2) is moved in such a way as to dispose the unit (3) in correspondence of the bottle which contains the selected liquid. The unit (3) is lowered by the actuator (Z1) until the respective jaws (31, 38) result in correspondence of the pipette (p) and relevant piston (SP). At this point, the said jaws (31, 38) are closed and the motor (39) started to lift the piston (SP) of an extent corresponding to the amount of liquid to be drawn. Following this, the unit (3) is lifted up to the initial level, so that the pipette (P) being tightened by the jaws (31) results lifted up as well. To this regard, it should be considered that the pipette (P) are merely resting with their collar (BC) upon the mouth of the bottles (B). At this point, the thus removed pipette (P), containing the liquid to be metered, is disposed in correspondence of the bottle (B) previously placed onto the adapter (66), as illustrated in FIG. 11-II, and the liquid is then introduced into the same bottle (B). Then, the unit (3) is moved away (FIG. 11-III), the table (63) (with the adapter (66) and bottle (B)) is lifted (see FIG. 11-IV), rotated through 180° (FIG. 11-V) and lowered back (FIG. 11-VI), so that the bottle (B) with the liquid put therein, results placed onto the stirrer (62) which drives the corresponding magnet (MB) into motion. Thereafter, the actuator (69) is operated so as to dispose the spout (67) onto the mouth of the bottle (B) (FIG. 11-VII). It is understood that the length of the rod (68) is suitably selected to allow a precise correspondence between the spout (67) and the mouth of the bottles (B) disposed onto the stirrer (62). Then, the delivery of the solvent (cold or hot water or other liquid) is operated by opening a solenoid valve (not shown in the drawings) while the solution in the course of formation is kept under constant agitation by the stirrer (66) which cooperates with the magnet (MB) disposed on the bottle (B) (FIG. 11-VIII, 11-IX). Once the desired amount of solvent has been introduced into the bottle (B), the actuator (69) is re-started to move the spout (67) back to the inoperative position and to release the bottle (B) (FIG. 11-X). Thereafter, the table (63) is again lifted (FIG. 11-XI), rotated through 180° (FIG. 11-XII) and lowered back (FIG. 11-XIII) so that the bottle (B), containing the required solution, can be withdrawn from the unit (4) (FIG. 11-XIV) and transferred up to the point of destination on the platform (1).

Figure 12:
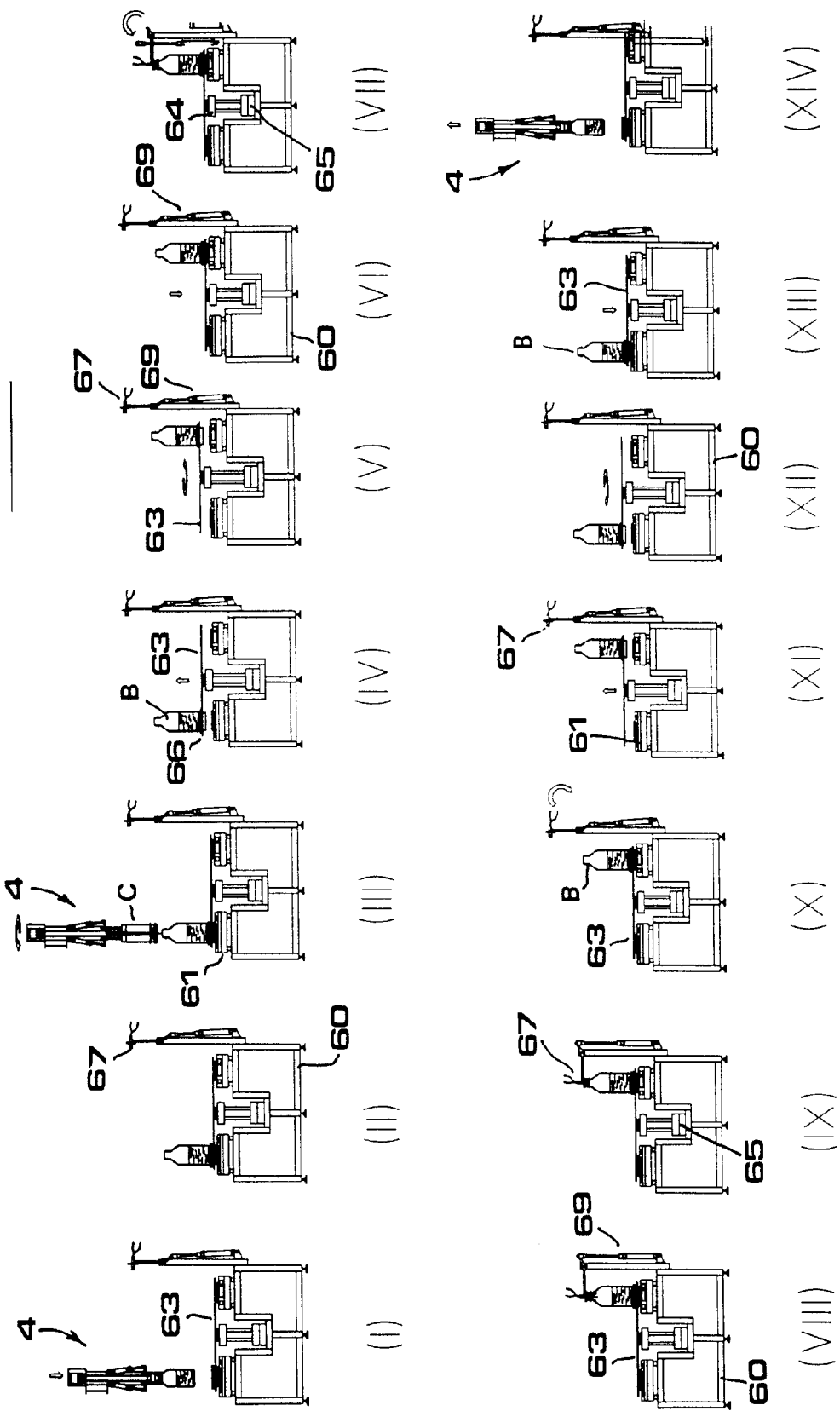
FIG. 12 shows schematically a succession of steps relating to the preparation of solutions starting from solid products.

A further example, referring to FIGS. 12-I/12-XIV of the attached drawings, relates to the preparation of solutions with solid products.

The carriage (2) is moved so as to have the unit (4) in correspondence of an empty and clean bottle, suitably disposed at a preset point of the platform (1). Then, the unit (4) is lowered by means of motor (Z1) and the said bottle (B) withdrawn and transported up to the adapter (66), as described with reference to the previous example (FIG. 12-I). Following this, the same unit (4) provides for picking up a bottle (B) to be replaced (that is, containing an expired or exhausted solution) and disposing it in place of the bottle (B) which has, in the meantime, been placed in the adapter (66). An operator will then provide for manually draw out the dirty bottle to replace it with a clean one. The unit (4), after having released the last engaged bottle, moves up as far as to result in correspondence of the container (C) containing the solid product selected for preparing the solution. Here the unit is moved down until the bush (44) results over the neck of the container (C), with the upper end (52) of rod (50) fitted into the takeoff (46) of the same unit (4). At this point, the actuators (42) are operated for clamping the container (C) between the jaws (41) of the unit (4), and the latter is lifted and transferred as far as to be correspondence of the bottle (B) disposed in the adapter (66). Afterwards, the motor (450) of unit (4) is started, so that the container (C) leaves out the solid product which, through the tube (53), falls into the bottle (B) (FIG. 12-III). The motor (450) rotates until the scale (66) senses an increase of weight of bottle (B) corresponding to the programmed dose of solid product to be introduced into the same bottle (B). Upon reaching this value, the motor (450) stops and the unit (4) is lifted and moved away from the bottle (B), after which the platform (63) is lifted (FIG. 12-IV), rotated through 180° (FIG. 12-V) and lowered again (FIG. 12-VI). The operating steps illustrated in FIGS. 12-VII to 12-XIV correspond to those described with reference to FIGS. 11-VII to 11-XIV and, thereby, will not be described once again.

Similarly, it is possible to withdraw, in a programmed sequence, liquid products and/or solutions by using the unit (3), and/or solid products by using the unit (4), and deliver these substances into one or more glasses (BI) located at a station (60) beside the one where the solvent is delivered, in order to form mixtures according to a programmed formula, starting from such substances. The said glasses weigh down onto a precision electronic scale which evaluates, upon each delivery, the corresponding change in weight, and feeds the relevant data to the central unit (UE) which acts as a control device by providing each time, likewise in the two examples previously dealt with, for comparing data coming from the scale with those stored in memory and related to different "recipes" to be prepared. The data thus collected and processed can be printed by a printer connected to the central unit (UE).

The above described system is completely self-contained and is able to operate without any interruption to carry out the preset work program, thereby making the required substances, solutions or mixtures, available all the time.

Practically, all the construction details may vary in any equivalent way as far as the shape, dimensions, elements disposition, nature of the used materials are concerned, without nevertheless departing from the scope of the adopted solution idea and, thereby, remaining within the limits of the protection granted to the present patent for industrial invention.

What is claimed is:

1. An apparatus for the automated preparation of solutions, the apparatus comprising:
   a combined metering system with a platform upon which it is possible to position a solid product container, a liquid product container, a solutions container, empty and clean bottle containers and a carriage movable onto the platform;
   bottle removal and handling means associated with the carriage for the removal and handling of the bottles and for the removal, handling and actuation of the solid product container, and
   preparation means for preparing solutions and/or mixtures starting from solid disposed in the solid product container.

2. An apparatus according to claim 1, further comprising liquid delivery and removal means, associated with the carriage, for the removal, handling and actuation of pipettes for the removal and delivery of the liquid products and the solutions, and the preparation means is also f r preparing the solutions and/or mixtures starting from liquid substances disposed in the liquid product container.

3. An apparatus according to claim 1 wherein the preparation means for preparing the solutions is provided at a corresponding station downstream of the platform.

4. An apparatus according to claim 2, further comprising programmable means for controlling the carriage, the liquid delivery and removal means for the removal, handling and actuation of the pipettes and said bottle removal and handling means for the removal and handling of the bottles and the removal, handling and actuation of the solid products container.

5. An apparatus according to claim 1 wherein said bottle removal and handling means for removing and handling the bottles and containers for the solid substances is supported by a structure fixed to the carriage, and comprises a clamp with two jaws operable by corresponding pneumatic actuators.

6. An apparatus according to claim 5, wherein said jaws are operable by said actuators via a system of levers hinged to each other and to a tubular skirt.

7. An apparatus according to claim 6, wherein said skirt ends up with a cylindrical bush of such diameter and height as to allow the positioning thereof onto the neck of bottles and containers.

8. An apparatus according to claim 7, wherein inside said tubular skirt a shall is provided associated with a corresponding electrical motor and terminating with a power takeoff complementarily shaped with respect to corresponding means for metering the solid products.

9. An apparatus according to claim 2, wherein said liquid delivery and removal means for the removal, handling and actuation of pipettes, comprises a clamp with two jaws operable by corresponding pneumatic actuators via a system of levers hinged to each other and to an outer skirt.

10. An apparatus according to claim 9, wherein said clamp comprises a second pair of jaws, disposed above the two jaws as upper jaws, each of said upper jaws being hinged to a dish borne by a worm screw having vertical axis and meshing with a lead nut supported by said skirt and associated with a motor.

11. An apparatus is according to claim 2 the preparation means for preparing the solutions is provided at a corresponding station downstream of the platform.

12. An apparatus according to claim 3, further comprising programmable means for controlling the carriage, the liquid delivery and removal means for the removal, handling and actuation of the pipettes and said bottle removal and handling means for the removal and handling of the bottles and the removal, handling and actuation of the solid products containers.

13. An apparatus according to claim 2 wherein said baffle removal and handling means for removing and handling the bottles and containers for the solid substances is supported by a structure fixed to the carriage, and comprises a clamp with two jaws operable by corresponding pneumatic actuators.

14. An apparatus according to claim 3 wherein said bottle removal and handling means for removing and handling the bottles and containers for the solid substances is supported by a structure fixed to the carriage, and comprises a clamp with two jaws operable by corresponding pneumatic actuators.

15. An apparatus according to claim 4 wherein said bottle removal and handling means for removing and handling the bottles and containers for the solid substances is supported by a structure fixed to the carriage, and comprises a clamp with two jaws operable by corresponding pneumatic actuators.

16. An apparatus according to claim 3, wherein said means for the removal, handling and actuation of pipettes, comprise a clamp with two jaws operable by corresponding pneumatic actuators via a system of levers hinged to each other and to an outer skirt.

17. An apparatus according to claim 4, wherein said liquid delivery and removal means for the removal, handling and actuation of pipettes, comprises a clamp with two jaws operable by corresponding pneumatic actuators via a system of levers hinged to each other.

18. An apparatus according to claim 5, wherein said liquid delivery and removal means for the removal, handling and actuation of pipettes, comprises a damp with two jaws operable by corresponding pneumatic actuators via a system of levers hinged to each other and to an outer skirt.

19. An apparatus according to claim 6, wherein said liquid delivery and removal means for the removal, handling and actuation of pipettes, comprises a clamp with two jaws operable by corresponding pneumatic actuators via a system of levers hinged to each other and to an outer skirt.

20. An apparatus according to claim 7, wherein said liquid delivery and removal means for the removal, handling and actuation of pipettes, comprises a clamp with two jaws operable by corresponding pneumatic actuators via a system of levers hinged to each other and to an outer skirt.

* * * * *